United States Patent [19]

Olson et al.

[11] 4,109,863

[45] Aug. 29, 1978

[54] APPARATUS FOR ULTRASONIC NEBULIZATION

[75] Inventors: Kenneth W. Olson; William J. Haas, Jr.; Velmer A. Fassel, all of Ames, Iowa

[73] Assignee: The United States of America as represented by the United States Department of Energy, Washington, D.C.

[21] Appl. No.: 825,519

[22] Filed: Aug. 17, 1977

[51] Int. Cl.² .......................... B05B 3/14; B05B 17/06
[52] U.S. Cl. .............................. 239/102; 128/DIG. 2; 261/DIG. 48; 239/128
[58] Field of Search .......................... 239/4, 102, 128; 128/194, DIG. 2; 261/DIG. 48; 310/341; 344

[56] References Cited

U.S. PATENT DOCUMENTS

| 3,291,122 | 12/1966 | Engstrom et al. | 128/DIG. 2 X |
|---|---|---|---|
| 3,392,916 | 7/1968 | Engstrom et al. | 239/102 |
| 3,433,461 | 3/1969 | Scarpa | 239/4 X |
| 3,729,138 | 4/1973 | Tysk | 239/102 |
| 3,812,854 | 5/1974 | Michaels et al. | 239/102 X |

*Primary Examiner*—Johnny D. Cherry
*Attorney, Agent, or Firm*—Dean E. Carlson; Frank H. Jackson; James W. Weinberger

[57] ABSTRACT

An improved apparatus for ultrasonic nebulization of liquid samples or suspensions in which the piezoelectric transducer is protected from chemical attack and erosion. The transducer is protected by being bonded to the inner surface of a glass plate which forms one end wall of a first hollow body provided with apparatus for circulating a fluid for cooling and stabilizing the transducer. The glass plate, which is one-half wavelength in thickness to provide an acoustically coupled outer nebulizing surface, seals an opening in a second hollow body which encloses an aerosol mixing chamber. The second body includes apparatus for delivering the sample solution to the nebulizing surface, a gas inlet for providing a flow of carrier gas for transporting the aerosol of the nebulized sample and an aerosol outlet.

5 Claims, 1 Drawing Figure

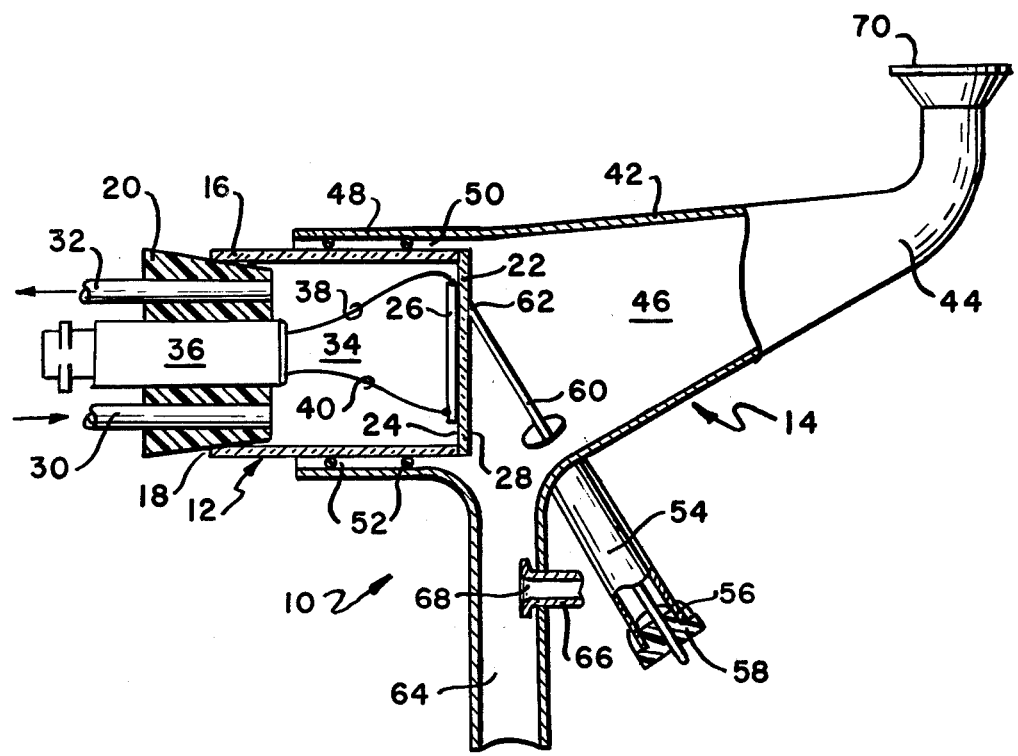

APPARATUS FOR ULTRASONIC NEBULIZATION

CONTRACTUAL ORIGIN OF THE INVENTION

The invention described herein was made in the course of, or under, a contract with the UNITED STATES ENERGY RESEARCH AND DEVELOPMENT ADMINISTRATION.

BACKGROUND OF THE INVENTION

This invention relates to a sample nebulization apparatus. More specifically, this invention relates to a new and improved ultrasonic nebulization apparatus for generating aerosols suitable for use in atomic spectroscopy, simulation of industrial and environmental atmospheres, for inhalation therapy or exposure, and for determination of filter efficiency.

Atomic spectroscopy, which includes atomic emission, absorption and fluorescence spectroscopy, requires that the sample for analysis, generally present in solution or suspension, be atomized or transformed into an aerosol so that the sample can be transported to an excitation source, such as a flame or plasma torch, where the sample is converted to atomic or ionic species for atomic spectroscopic analysis.

Pneumatic nebulization has generally been used for aerosol formation for analytical purposes. However, the use of pneumatic nebulization has a number of drawbacks which affect aerosol formation and which may have an adverse effect upon the analytical results obtained with the method. For example, pneumatic nebulization is often very inefficient, only about 1% of the sample volume actually reaching the atomic spectroscopy excitation source. Effective nebulization and droplet formation require a high rate of flow of nebulizing gas. However, since the nebulizing gas is also the aerosol carrier gas, the flow rate is too high for some excitation sources such as plasmas. A high flow rate will also impact some of the aerosol on the walls of the chamber, resulting in loss of sample. Pneumatic nebulizers that operate at low flow rates have been developed, but their efficiency of nebulization is low and they have a tendency to clog. Solid materials which may be present in sample solutions or suspensions often cause clogging of pneumatic nebulizers. In this event, the nebulizer-spray chamber apparatus usually has to be disassembled and cleaned in order to regain optimum nebulizer performance.

Ultrasonic nebulizers possess a number of attractive characteristics. First, the rate of aerosol production at the transducer does not depend on the carrier-gas flow as it does in pneumatic nebulizers. Thus the aerosol production rate and the carrier-gas flow rate may be varied independently. Second, ultrasonic nebulizers can produce aerosols of greater number density and of more uniform particle size than pneumatic nebulizers. Third, the mean size of the particle produced by an ultrasonic nebulizer is frequency dependent; smaller particles can be produced by increasing the ultrasonic frequency employed. The advantage gained is that smaller particles are more efficiently transported and are more rapidly desolvated and atomized in the excitation cell.

Two types of ultrasonic nebulizers have generally been used with atomic spectroscopy excitation sources. In continuous feed ultrasonic nebulizers, the analyte solution is continuously pumped onto either the transducer surface or transfer plate, directly connected to a transducer, where the analyte is nebulized by direct impingement. These nebulizers are preferred for routine analysis because rapid sample interchange can be achieved and because the sample cleanout time, necessary to avoid memory effects or the reintroduction of a previous analyte, is acceptably short. Solutions of high salt content or of high acidity or alkalinity have been found, however, to attack the transducer, even when various protective coatings were employed. The use of O-ring sealed transfer plates to nebulize the analyte and protect the transducer has also been tried, but this approach either suffers from seal failure, where the analyte ultimately reaches and attacks the transducer, or from incompatibilities between the analyte plate material and analyte ions in the sample solution. In batch type ultrasonic nebulizers, the ultrasonic energy is coupled to a known initial volume of analyte solution, either directly or through an inert liquid or solid interface, thus circumventing the corrosion problem. These nebulizers suffer from other experimental shortcomings, however. Foremost among these are inconvenient sample change capability and memory effects.

SUMMARY OF THE INVENTION

We have found that, by mounting the transducer on one face of a glass plate, about one-half wavelength in thickness, the other face of the plate provides an excellent acoustically coupled nebulizing surface. We have further found that, by fusing the plate to the end of a container which is provided with a flow of cooling fluid, we are able to protect the transducer from chemical attack and sample erosion while achieving long-term transducer stability. We have also found that, by proper sample tube placement and carrier-gas inlet design, we have been able to minimize memory effects, minimize pulsing of the sample aerosol, and generally obtain better results. In the apparatus of our invention, the ultrasonic transducer is bonded to the inner face of a glass plate which is about one-half wavelength in thickness to provide an acoustically coupled outer nebulizing surface and which forms one end of a first hollow body. The other end of the body is removably sealed and provided with means for circulating a cooling fluid through the body for cooling and stabilizing the transducer and with connecting means for providing an electrical signal to activate the transducer. The first body is sealed into an opening in a second hollow body which encloses an aerosol mixing chamber so that the nebulizing surface extends into the chamber. The second body also includes means for delivering the sample to be nebulized to the nebulizing surface, means for providing a supply of carrier-gas to the chamber for transporting the aerosol of nebulized sample, and means for removing the aerosol from the chamber.

It is therefore an object of the invention to provide an apparatus which utilizes an ultrasonic transducer for nebulizing samples and forming aerosols.

It is another object of the invention to provide an apparatus which utilizes an ultrasonic transducer for nebulizing samples and forming aerosols in which the transducer is protected from chemical attack and erosion.

Finally, it is the object of the invention to provide an apparatus for nebulizing samples and forming aerosols in which the problems of memory effect and aerosol pulsing are minimized.

BRIEF DESCRIPTION OF THE DRAWINGS

The FIGURE is a longitudinal view partially in cross-section of the apparatus of the invention.

DETAILED DESCRIPTION OF THE PREFERRED EMBODIMENT

Referring now to the drawing, the apparatus 10 of the invention consists of a nebulizer assembly 12 and an aerosol-forming assembly 14. Assembly 12 consists of a hollow cylindrical body 16, having a first open end 18 sealed by a removable plug 20 and a second end enclosed by a flat glass plate 22 to form a unitary structure. Plate 22 has an inner surface 24 to which an ultrasonic transducer 26 is adhesively bonded and is approximately one-half wavelength in thickness with respect to the fundamental operating frequency of the transducer so that outer surface 28 is acoustically coupled to the transducer 26, forming a nebulizing surface. Removable plug 20 is penetrated by coolant inlet 30 and outlet 32 and provided with means (not shown) for circulating a flow of fluid through a cooling chamber 34 in body 16 for cooling transducer 26. A signal is supplied from a source of RF energy (not shown) through electrical connector 36 in plug 20 and leads 38 and 40 to transducer 26. The aerosol-forming assembly 14 consists of an elongated hollow body 42 having a conically shaped end 44 enclosing a mixing chamber 46 and an open cylindrically shaped end 48 forming a receiving chamber 50 into wich nebulizer assembly 12 is positioned so that the nebulizing surface 28 extends almost to mixing chamber 46. Assembly 12 is sealed in chamber 50 by a pair of "O" ring seals 52. Radiating outward and downward from the wall of body 42 is hollow inlet arm 54 having an open end 56 sealed by removable plug 58. Penetrating plug 58 and extending upward through inlet arm 54 into the chamber 46 is sample inlet tube 60 having an outlet end 62 cut so that the end is parallel to surface 28 and positioned so that the end is adjacent or just touches nebulizing surface 28 for supplying sample to be nebulized. Extending downward from the wall of body 42 beneath nebulizing surface 28 is a vertical drain tube 64 for draining condensed or unnebulized sample from the chamber 46. Just below body 42, drain tube 64 is penetrated by a short horizontal inlet tube 66 for introducing a flow of carrier gas into chamber 46 for forming an aerosol. Tube 66 terminates in a flared outlet end 68 within the drain tube to prevent the collection of condensate in the end of the inlet and to permit a smooth flow of carrier gas into chamber 46. A vertical aerosol outlet 70 in the upper wall of conically shaped end 44 completes the assembly.

Plate 22 is preferably flat and may be of fused quartz or any glass which is resistant to chemical damage by the sample solution and which will transmit ultrasonic vibrations from transducer 26 to outer surface 28 to nebulize the solutions. Borosilicate glass and fused silica glass have been found to perform satisfactorily, although other glass compositions may also be suitable. It is important that plate 22 be sealed, preferably by fusing to the end of body 16, which preferably is of the same material as the plate, to prevent any penetration of sample solution into cooling chamber 34 where it may ultimately contact and damage or destroy the transducer. It is also important that the thickness of the plate be about one-half wavelength with respect to the fundamental frequency of the transducer in order to provide maximum acoustical coupling to the nebulizing surface of the plate and to prevent separation of the transducer from the inner face of the plate. The determination of plate thickness is known in the art and is dependent on transducer frequency and the glass composition. Thus, for example, a transducer with a frequency of about 3 MHz requires a fused silica plate 1 mm thick, while a transducer frequency of 1.4 MHz requires 2 mm of borosilicate glass.

The transducer may be any piezoelectric generating element known in the art which vibrates in a thickness mode such as, for example, a ceramic wafer of lead zirconate titanate, barium titanate, or quartz. The transducer may be mounted on the inner face of the plate by any well-known bonding agents having good acoustic conducting properties such as Eccobond 55 ® supplied by Emerson-Cumming & Co., Canton, Mass.

Long-term transducer stability is ensured by cooling the transducer by a flow of cooling fluid through the first hollow body. While any nonconductive fluid is suitable for the purpose, deionized water is preferred.

Sample tube 60 is placed so that only the outlet end 62 is adjacent or just touching nebulizing surface 28, preferably near the top portion of the disc, to increase sample nebulization as the sample flows down over face 28 and to prevent any dampening effect the tube may have on the nebulizing surface. The memory effect from any previous samples is minimized by placing outlet end 62 higher than tube 60 so that any unnebulized or condensed nebulized sample will flow down tube 60 away from nebulizing surface 28, preventing it from being reintroduced onto the nebulizing surface. The precise angle of the tube is not important, only that it be adequate to cause any condensate on the tube to drain away from the nebulizing surface.

Aerosol pulsing is minimized by flaring the outlet end 68 of gas inlet 66 within drain tube 64 to prevent any possibility of condensate collecting in the opening of the tube which will block the smooth flow of carrier gas into the mixing chamber.

While not necessary for the satisfactory utilization of the apparatus of the invention for atomic spectroscopy, it has been found advantageous to incorporate the addition of a desolvation apparatus of a type well known in the art into the aerosol outlet line before introduction of the aerosol into an excitation source such as a flame or an inductively coupled plasma. For other applications, however, such as in the simulation of industrial atmospheres, for which dry, solid particles may be desired, the desolvation apparatus is clearly required.

EXAMPLE

In order to determine the effectiveness of the apparatus of the invention, a comparison was made to determine detection levels for the simultaneous multielement determination for sample aerosols generated by the nebulizer with a pneumatic nebulizer and incorporating an inductively coupled plasma as an excitation source.

The ultrasonic nebulizer was as described herein, and consisted of a Channel Products, Inc., Model CPMT, lead zirconate titanate transducer having a frequency of 1.45 MHz. The transducer was bonded to the inside of a Corning 7740 glass end plate which had been fused to one end of a 2 inch long, 1.5 inch O.D. hollow glass cylinder. The sample introduction rate was 2.8 ml/min using a peristaltic pump.

The pneumatic nebulizer was locally designed and constructed of teflon and glass using a 2.8 ml/min sample uptake rate for an aerosol argon flow rate of 1 liter/-min.

The polychrometer was a Model QVAC 127 ARL.

Detection limits were determined for a representative set of 14 elements of bio-environmental interest in 1% HNO, 1% NaCl and 1/1 HNO /deionized water solutions. Three different sample introduction arrangements were employed using pneumatic nebulization without aerosol desolvation, pneumatic nebulization with desolvation and ultrasonic nebulization with desolvation. All operating conditions such as sample intake rate, aerosol carrier gas and plasma coolant gas rates, plasma power and observation height, etc. were maintained at identical values for these determinations. The results from these determinations are shown in the table below and clearly show that the described apparatus provides powers of detection clearly superior to those obtained with one type of pneumatic nebulizer, either with or without aerosol desolvation.

Inductively Coupled Plasma - Atomic Emission Spectroscopy Detection Limits for Simultaneous Multielement Determination (ug/l)

| | Pneumatic Nebulization | | Ultrasonic |
|---|---|---|---|
| Desolvation | No | Yes | Yes |
| Al | 7. | 4. | 0.4 |
| As | 30. | 20. | 2. |
| Cd | 1. | 2. | 0.07 |
| Co | 2. | 2. | 0.1 |
| Cr | 2. | 0.9 | 0.08 |
| Cu | 2. | 0.8 | 0.04 |
| Fe | 7. | 4. | 0.5 |
| Mn | 0.2 | 0.1 | 0.01 |
| Mo | 5. | 4. | 0.3 |
| Ni | 10. | 8. | 0.3 |
| Pb | 20. | 10. | 1. |
| Se | 20. | 10. | 1. |
| V | 2. | 2. | 0.09 |
| Zn | 2. | 3. | 0.1 |

Measurements of the efficiency of nebulization for the pneumatic and ultrasonic nebulizer systems were obtained from the ratio of the amount of desolvated analyte which entered the plasma torch to the amount of analyte aspirated. The results were $11.0 \pm 0.4$ percent for the ultrasonic nebulizer and $1.08 \pm 0.13$ percent for the pneumatic nebulizer. The sample uptake rate was the same for both nebulizers, so the measured efficiencies are equivalent to the relative rates of delivery of sample aerosol to the plasma torch. The ten-fold greater sample delivery rate provided by the ultrasonic nebulizer corresponds almost exactly to the degree of improvement in detection limits which was observed for ultrasonic pneumatic nebulization.

As can be seen from the discussion and example, the apparatus of the invention provides a novel and effective way to eliminate ultrasonic transducer destruction and provides an efficient and effective apparatus for preparing aerosols.

The embodiments of the invention in which an exclusive property or privilege is claimed are defined as follows:

1. A sample nebulizing system for nebulizing a liquid sample or suspension into a carrier gas to form an aerosol comprising:

a. a first hollow body having a first open end and a second end enclosed by a flat plate selected from the group consisting of glass and fused quartz, the plate having an inner face within the body and an outer nebulizing face;

b. ultrasonic transducer means bonded to the inner face of the plate for transmitting ultrasonic vibrations to the nebulizing face;

c. sealing means in the open end of the first body for enclosing a cooling chamber;

d. coolant circulating means in the sealing means for passing a coolant through the chamber for cooling the transducer means;

e. a second hollow body enclosing an aerosol mixing chamber, the body having an opening for receiving the enclosed end of the first body including means for sealing the first body in the opening;

f. sample delivery means in the second body for delivering a sample to the nebulizing face to be nebulized into the mixing chamber;

g. carrier gas inlet means in the second body for introducing a carrier gas into the mixing chamber to transport an aerosol of the nebulized sample;

h. an aerosol outlet in the second body for removing the aerosol from the mixing chamber; and i. drain means in the second body for removing condensed aerosol and unnebulized sample from the mixing chamber.

2. The system of claim 1 wherein the plate is about one-half wavelength in thickness with respect to the fundamental frequency of the transducer means, the first hollow body is selected from the group consisting of glass and fused quartz and the plate is fused to the first body.

3. The system of claim 2 wherein the sample delivery means is a tube having an outlet end, the tube penetrating the second hollow body at an upward angle, the outlet end being positioned adjacent the nebulizing face whereby any condensed sample will run down the tube away from the nebulizing face.

4. The system of claim 3 wherein the drain means is a tube in the second body extending vertically downward below the mixing chamber.

5. The system of claim 4 wherein the carrier gas inlet means is a short horizontal tube which penetrates the drain tube a short distance below the second body, and has a flared end within the drain tube for preventing the collection of condensate within the gas inlet tube.

* * * * *